United States Patent [19]

VandenBerg

[11] Patent Number: Plant 6,944

[45] Date of Patent: Jul. 25, 1989

[54] CHRYSANTHEMUM PLANT NAMED TASCA

[75] Inventor: Cornelis P. VandenBerg, Salinas, Calif.

[73] Assignee: Yoder Brothers, Inc., Barberton, Ohio

[21] Appl. No.: 218,984

[22] Filed: Jul. 14, 1988

[51] Int. Cl.[4] ..... A01H 5/00
[52] U.S. Cl. ..... Plt./74
[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Tasca particularly characterized by its flat capitulum form; anemone capitulum type; red-purple ray floret color with a red-purple to greyed-purple anemone cushion; diameter across face of capitulum of up to 7 cm at maturity when grown as a pinched spray pot mum with a diameter of anemone cushion of up to 3.2 cm; uniform eight week photoperiodic flowering response to short days; short plant height when grown as a pinched pot mum; and semi-spreading and prolific branching pattern.

3 Drawing Sheets

The present invention comprises a new and distinct cultivar of Chrysanthemum, botanically known as *Dendranthema grandiflora,* and referred to by the cultivar name Tasca.

Tasca, identified as 84421005, was originated from a cross made in a controlled breeding program in Salinas, Calif. in 1984.

The female parent of Tasca was the cultivar identified as Donos, disclosed in U.S. Plant patent application Ser. No. 920,163. The male parent of Tasca was the cultivar identified as Chic, disclosed in U.S. Plant Pat. No. 5,660.

Tasca was discovered and selected as one flowering plant within the progeny of the stated cross by Cornelis P. VandenBerg in April 1985 in a controlled environment in Salinas, Calif.

The first act of asexual reproduction of Tasca was accomplished when vegetative cuttings were taken from the initial selection in June 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Tasca are firmly fixed and are retained through successive generations of asexual reproduction.

Tasca has not been observed under all possible environmental conditions. The phenotype may vary significantly with variations in environment such as temperature, light intensity, and daylength.

The following observations, measurements and comparisons describe plants grown in Salinas, Calif. and Leamington, Canada under greenhouse conditions which approximate those generally used in commercial greenhouse practice.

The following traits have been repeatedly observed and are determined to be basic characteristics of Tasca, which, in combination, distinguish this Chrysanthemum as a new and distinct cultivar:

1. Flat capitulum form.
2. Anemone capitulum type.
3. Red-purple ray floret color, with a red-purple to greyed-purple anemone cushion.

4. Diameter across face of capitulum up to 7 cm at maturity, with a diameter of anemone cushion of up to 3.2 cm when grown as a pinched spray pot mum.
5. Uniform eight week photoperiodic flowering response to short days.
6. Short plant height, requiring 7 to 14 long days after pinch prior to short days and 1 application of 2500 ppm B-9 to attain a flowered plant height of 25 to 35 cm for year-round flowerings when grown as a pinched pot mum.
7. Branching pattern is spreading and prolific.

The accompanying photographic drawings show typical inflorescence and leaf characteristics of Tasca, with the colors being as nearly true as possible with illustrations of this type.

Sheet 1 is a color photograph of Tasca grown as a pinch spray pot mum.

Sheet 2 is a black and white photograph of three views of the inflorescence of Tasca.

Sheet 3 is a black and white photograph showing the upper and under sides of the leaves of Tasca at three stages of development (mature, intermediate and immature).

Of the commercial cultivars known to the inventor, the most similar in comparison to Tasca is the cultivar Rave, disclosed in U.S. Plant Pat. No. 5,738. Reference is made to Chart A, which compares certain characteristics of Tasca to the same characteristics of Rave.

Similar traits are capitulum form and type, and flowering response period. Ray floret color of Tasca is more red-purple than the color of Rave. Tasca has a more spreading and prolific branching pattern, a larger diameter of capitulum, and a shorter plant height than Rave.

In the following description, color references are made to the Royal Horticultural Society Colour Chart. The color values were determined on plant material grown as a pinched spray pot mum in Salinas, Calif. on Mar. 16, 1988.

Classification:

*Botanical.—Dendranthema grandiflora,* cv Tasca.
*Commercial.*—Anemone spray pot mum.

INFLORESCENCE

A. Capitulum:

*Form.*—Flat.
*Type.*—Anemone.
*Diameter across face.*—Up to 7 cm at maturity.
*Diameter of anemone cushion.*—Up to 3.2 cm.

B. Corolla of ray florets:
*Color (general tonality from a distance of three meters).*—Red-purple.
*Color (upper surface).*—70C to 70D, slightly tinged with 75B.
*Color (under surface).*—70D, slightly tinged with 75B.
*Shape.*—Flat, oblong.

C. Corolla of disc florets (Anemone Cushion):
*Color (mature).*—Closest to 186A, overcast with 59B.
*Color (immature).*—Closest to 59A.

D. Reproductive organs:
*Androecium.*—Present on disc florets only; no pollen.
*Gynoecium.*—Present on both ray and disc florets.

PLANT

A. General appearance:
*Height.*—Short; 25 to 35 cm as a pinched spray pot mum with 7 to 14 long days after pinch prior to short days and 1 application of 2500 ppm B-9 SP.
*Branching pattern.*—Spreading and prolific.

B. Foliage:
*Color (upper surface).*—147A.
*Color (under surface).*—147B.
*Shape.*—Lobed and serrated.

CHART A

COMPARISON OF TASCA AND RAVE

| | Tasca | Rave |
|---|---|---|
| Ray floret color | Red purple | Purple violet |
| Capitulum form and type | Flat Anemone | Flat Anemone |
| Branching pattern | Spreading and prolific | Semi-spreading |
| Diameter across face of capitulum | Up tp 7 cm | 5 to 6 cm |
| Plant height | Short | Medium |
| Flowering response period | 8 weeks | 7 to 8 weeks |

COMPARISONS MADE OF PLANTS GROWN AS PINCHED SPRAY POT MUMS IN SALINAS, CALIFORNIA

I claim:

1. A new and distinct Chrysanthemum plant named Tasca, as described and illustrated.

* * * * *

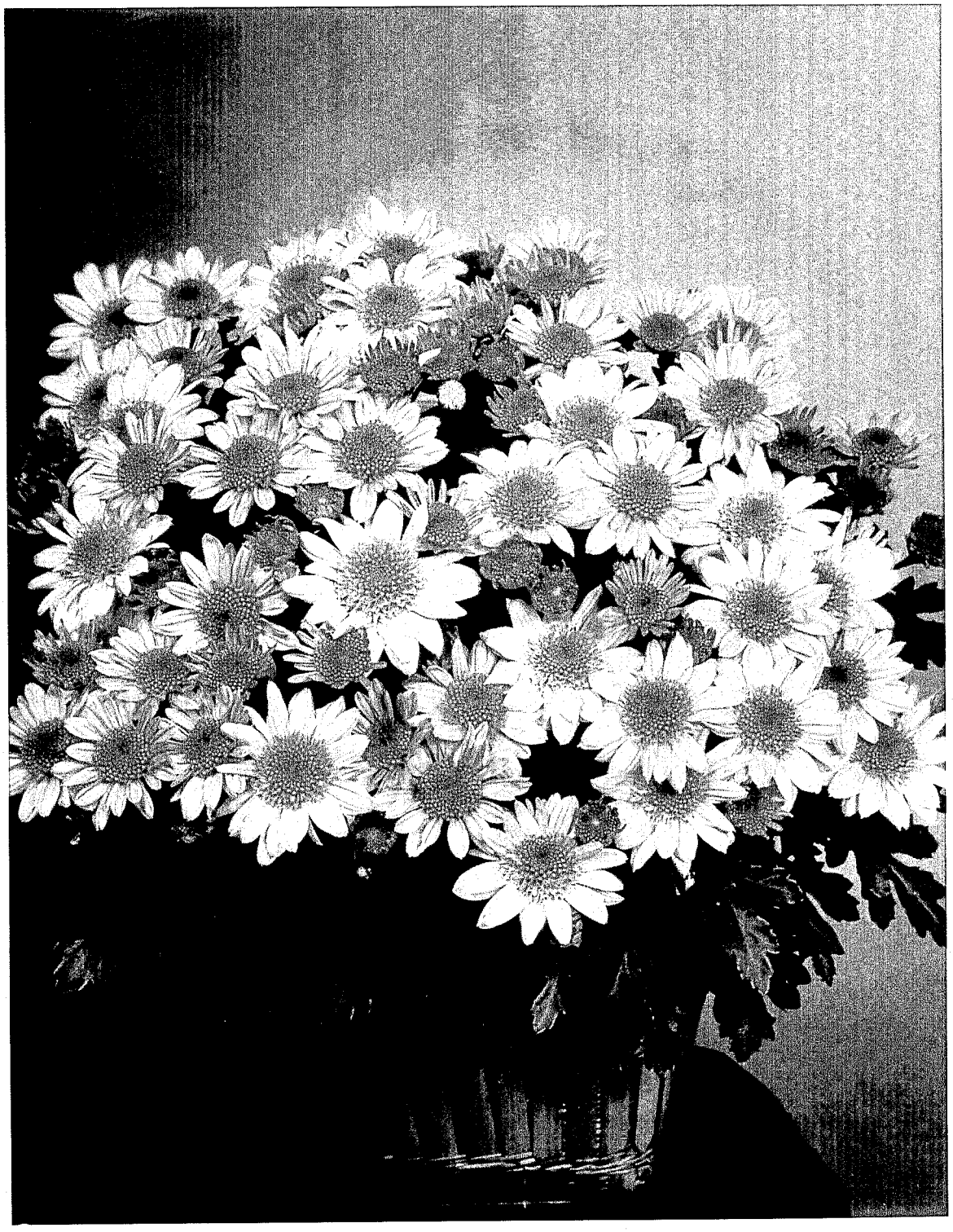

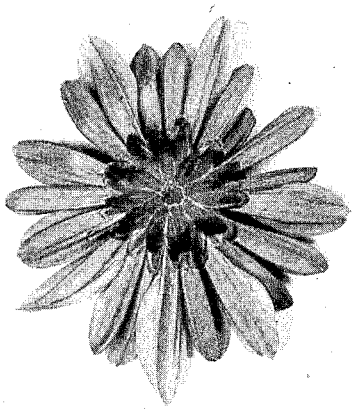
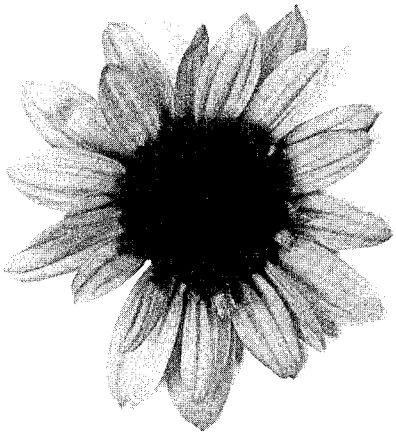
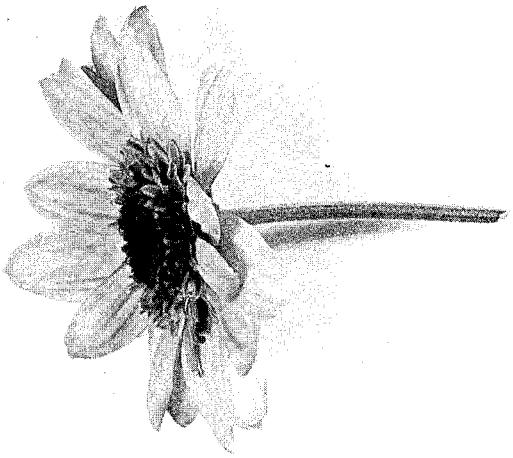

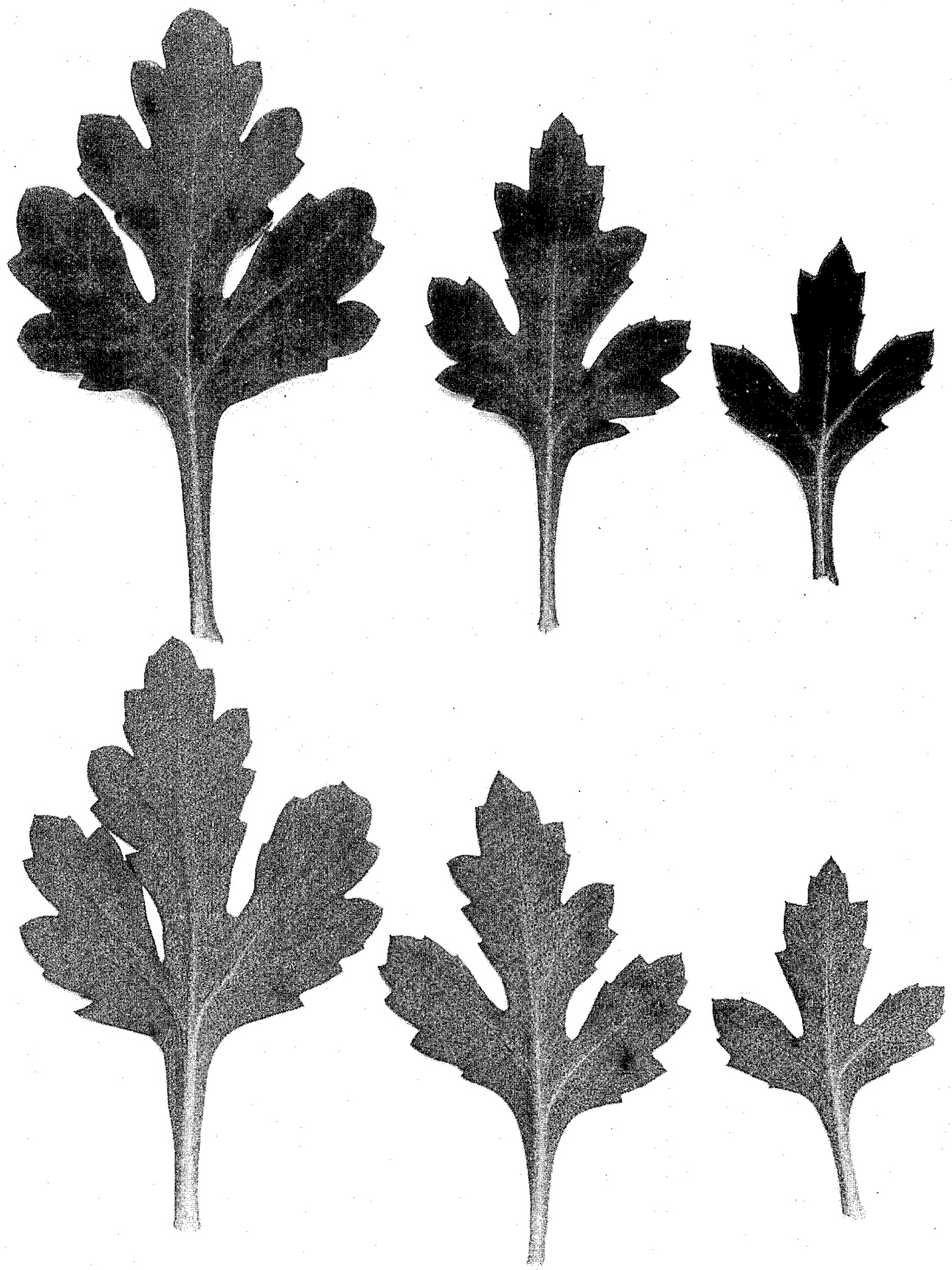

UNITED STATES PATENT AND TRADEMARK OFFICE

CERTIFICATE OF CORRECTION

PATENT NO. : Plant 6,944

DATED : July 25, 1989

INVENTOR(S) : Cornelis P. VandenBerg

It is certified that error appears in the above—identified patent and that said Letters Patent is hereby corrected as shown below:

Column 2, line 8, after "B-9" insert --SP--.

Signed and Sealed this

Twelfth Day of March, 1991

*Attest:*

HARRY F. MANBECK, JR.

*Attesting Officer*

*Commissioner of Patents and Trademarks*